US008703306B2

(12) United States Patent
Groeger et al.

(10) Patent No.: US 8,703,306 B2
(45) Date of Patent: Apr. 22, 2014

(54) METHOD FOR APPLYING A POLYMER COATING TO AN INTERNAL SURFACE OF A CONTAINER

(75) Inventors: Joseph H. Groeger, Storrs, CT (US); Hans-Jurgen Neugebauer, Warburg (DE); Christoph Schulte, Paderborn (DE)

(73) Assignee: Presspart GmbH & Co. KG, Marsberg (DE)

( * ) Notice: Subject to any disclaimer, the term of this patent is extended or adjusted under 35 U.S.C. 154(b) by 102 days.

(21) Appl. No.: 13/531,869

(22) Filed: Jun. 25, 2012

(65) Prior Publication Data

US 2012/0288646 A1 Nov. 15, 2012

Related U.S. Application Data

(63) Continuation of application No. 11/952,652, filed on Dec. 7, 2007, now Pat. No. 8,227,027.

(51) Int. Cl.
*C03C 17/22* (2006.01)
*C04B 41/52* (2006.01)
*A61F 2/00* (2006.01)
*A61B 19/02* (2006.01)

(52) U.S. Cl.
CPC .............. *C04B 41/52* (2013.01); *C03C 17/22* (2013.01); *A61F 2/0095* (2013.01); *A61B 19/026* (2013.01)
USPC ........................... 428/698; 428/704; 206/438

(58) Field of Classification Search
CPC ....... C03C 17/22; C04B 41/52; A61F 2/0095; A61B 19/026
USPC .................................... 428/698, 704; 206/438
See application file for complete search history.

(56) References Cited

U.S. PATENT DOCUMENTS

| | | |
|---|---|---|
| 2,562,118 A | 7/1951 | Osdal |
| 2,815,889 A | 12/1957 | Stetz et al. |
| 2,886,217 A | 5/1959 | Thiel |
| 3,330,769 A | 7/1967 | Golben et al. |
| 3,611,990 A | 10/1971 | Paoletti et al. |
| 3,896,602 A | 7/1975 | Petterson |
| 3,929,537 A | 12/1975 | Erwin |
| 3,962,171 A | 6/1976 | Robbins |
| 3,996,182 A | 12/1976 | Hong et al. |
| 4,087,026 A | 5/1978 | Petterson |
| 4,125,152 A | 11/1978 | Kestner et al. |
| 4,143,204 A | 3/1979 | Fang |
| 4,180,609 A | 12/1979 | Vassiliou |
| 4,285,937 A | 8/1981 | Kalvoda |
| 4,339,483 A | 7/1982 | Ueno et al. |
| 4,710,232 A | 12/1987 | Tahbaz |
| 4,741,934 A | 5/1988 | Terayama et al. |
| 4,762,254 A | 8/1988 | Nitta |
| 4,819,834 A | 4/1989 | Thiel |
| 4,861,647 A | 8/1989 | Ishikawa et al. |
| 4,897,439 A | 1/1990 | Rau et al. |
| 4,902,318 A | 2/1990 | Stevens et al. |
| 4,945,008 A | 7/1990 | Heyes et al. |
| 4,961,966 A | 10/1990 | Stevens et al. |
| 4,980,210 A | 12/1990 | Heyes |
| 5,006,383 A | 4/1991 | Achille et al. |
| 5,043,191 A | 8/1991 | Endres et al. |
| 5,149,717 A | 9/1992 | Von Sprecher et al. |
| 5,158,710 A | 10/1992 | VanEenam |
| 5,168,107 A | 12/1992 | Tannenbaum |
| 5,196,134 A | 3/1993 | Jackson |
| 5,221,576 A | 6/1993 | Bosc et al. |
| 5,225,183 A | 7/1993 | Purewal et al. |
| 5,290,539 A | 3/1994 | Marecki |
| 5,340,463 A | 8/1994 | Layre et al. |
| 5,349,947 A | 9/1994 | Newhouse et al. |
| 5,468,798 A | 11/1995 | Leech |
| 5,496,585 A | 3/1996 | Hamilton et al. |
| 5,536,583 A | 7/1996 | Roberts et al. |
| 5,674,592 A | 10/1997 | Clark et al. |
| 5,676,929 A | 10/1997 | Akehurst et al. |
| 5,683,676 A | 11/1997 | Akehurst et al. |
| 5,721,309 A | 2/1998 | Sharma et al. |

(Continued)

FOREIGN PATENT DOCUMENTS

| | | |
|---|---|---|
| CA | 2 130 867 | 2/1995 |
| DE | 1 226 251 | 10/1966 |

(Continued)

OTHER PUBLICATIONS

Fluorine-containing Polymers, Polytetrafluorethylene, pp. 332-351.
Pharmaceutical—A guide to pharmaceutical aerosol containers, Presspart (no date).
Parsons et al., The use of surface energy and polarity determinations to predict physical stability of non-polar, non-aqueous suspensions, International Journal of Pharmaceutics, vol. 83, pp. 163-170, (1992).
Plasma Deposited Silica Coatings for High Barrier Film and Rigid Containers, John T. Felts, pp. 147-163, COEX 1989.
The Aerosol Handbook $2^{nd}$ Edition, Montfort A. Johnsen, The Technology of Metal Aerosol Containers, pp. 63-64 and p. 175 (1982).

(Continued)

*Primary Examiner* — Betelhem Shewareged
(74) *Attorney, Agent, or Firm* — Carmody Torrance Sandak & Hennessey LLP

(57) ABSTRACT

A method of cleaning and coating at least one surface of a container for storing a medicament or other ingestible non-pharmaceutical product, the method comprising the steps of using a water-based cleaning composition in conjunction with a water-based crosslinked acrylic resin containing coating material. The process makes the cleaning and coating technology consistent with present environmental regulations and workplace safety requirements, including control of emissions of volatile organic compounds (VOCs). Further, the concentration of extractible organic compounds has been reduced to the lowest practical level. The process is also applicable to other substrates where it is desired to have low-extractable organics and high adhesion of the subsequently applied coating.

10 Claims, No Drawings

(56) References Cited

U.S. PATENT DOCUMENTS

| | | | |
|---|---|---|---|
| 5,725,678 | A | 3/1998 | Cannon et al. |
| 5,728,660 | A | 3/1998 | Borah |
| 5,932,020 | A | 8/1999 | Murphy |
| 6,113,008 | A | 9/2000 | Arsenault et al. |
| 6,119,853 | A | 9/2000 | Garrill et al. |
| 6,149,892 | A | 11/2000 | Britto |
| 6,179,118 | B1 | 1/2001 | Garrill et al. |
| 6,253,762 | B1 | 7/2001 | Britto |
| 6,315,112 | B1 | 11/2001 | Garrill et al. |
| 6,315,985 | B1 | 11/2001 | Wu et al. |
| 6,352,152 | B1 | 3/2002 | Anderson et al. |
| 6,390,291 | B1 | 5/2002 | Garrill et al. |
| 6,511,652 | B1 | 1/2003 | Ashurst et al. |
| 6,511,653 | B1 | 1/2003 | Britto et al. |
| 6,517,940 | B1 | 2/2003 | Millero et al. |
| 6,532,955 | B1 | 3/2003 | Ashurst et al. |
| 6,546,928 | B1 | 4/2003 | Ashurst et al. |
| 6,596,260 | B1 | 7/2003 | Brugger et al. |
| 6,610,273 | B2 | 8/2003 | Wu et al. |
| 6,626,170 | B1 | 9/2003 | Barnes et al. |
| 6,716,414 | B2 | 4/2004 | Lewis et al. |
| 6,905,550 | B2 | 6/2005 | Labib |
| 7,015,262 | B2 | 3/2006 | Leong |
| 7,018,618 | B2 | 3/2006 | Lewis et al. |
| 7,037,584 | B2 | 5/2006 | Wind et al. |
| 7,205,026 | B2 | 4/2007 | Groeger et al. |
| 7,223,381 | B2 | 5/2007 | Lewis et al. |
| 7,347,199 | B1 | 3/2008 | Lewis et al. |
| 7,381,402 | B2 | 6/2008 | Lewis et al. |
| 2003/0089369 | A1 | 5/2003 | Lewis et al. |
| 2003/0196685 | A1* | 10/2003 | Anzures et al. ............ 134/22.19 |
| 2004/0033201 | A1 | 2/2004 | Wu et al. |
| 2004/0096399 | A1 | 5/2004 | Lewis et al. |
| 2004/0126325 | A1 | 7/2004 | Lewis et al. |
| 2004/0222244 | A1 | 11/2004 | Groeger |
| 2004/0242451 | A1 | 12/2004 | Ketelson et al. |
| 2005/0142071 | A1 | 6/2005 | Lewis et al. |
| 2005/0220717 | A1 | 10/2005 | Wu et al. |
| 2006/0083879 | A1 | 4/2006 | Brewis et al. |
| 2006/0228570 | A1 | 10/2006 | Burns et al. |
| 2007/0184997 | A1 | 8/2007 | Hino et al. |
| 2008/0115782 | A1 | 5/2008 | Lewis et al. |

FOREIGN PATENT DOCUMENTS

| | | | |
|---|---|---|---|
| DE | 40 09 397 | A1 | 9/1991 |
| EP | 0 273 980 | A1 | 7/1988 |
| EP | 0 297 712 | A2 | 1/1989 |
| EP | 0 317 865 | A2 | 5/1989 |
| EP | 0 384 606 | A1 | 8/1990 |
| EP | 0 465 741 | A1 | 1/1992 |
| EP | 0 487 200 | A1 | 5/1992 |
| EP | 0 504 112 | A2 | 9/1992 |
| EP | 0 561 987 | B1 | 9/1993 |
| EP | 0 338 670 | B1 | 11/1994 |
| EP | 0 642 992 | A2 | 3/1995 |
| EP | 0 561 981 | B1 | 1/1996 |
| EP | 0 820 322 | B1 | 7/2002 |
| EP | 1 241 113 | A1 | 9/2002 |
| EP | 1 523 975 | A2 | 4/2005 |
| EP | 1 523 975 | A3 | 4/2005 |
| EP | 1 131 051 | B1 | 1/2006 |
| EP | 1 666 029 | A1 | 6/2006 |
| EP | 1 674 079 | A2 | 6/2006 |
| EP | 1 368 253 | B1 | 3/2008 |
| FR | 2 267 496 | | 11/1975 |
| GB | 1 191 700 | | 5/1970 |
| GB | 1 228 438 | | 4/1971 |
| GB | 1 322 084 | | 7/1973 |
| GB | 1 362 495 | | 8/1974 |
| GB | 1 394 327 | | 5/1975 |
| GB | 2 003 415 | A | 3/1979 |
| GB | 2 077 229 | A | 12/1981 |
| GB | 2 214 891 | A | 9/1989 |
| GB | 2 216 794 | A | 10/1989 |
| JP | 59-174479 | | 10/1984 |
| JP | 63-178038 | | 7/1988 |
| JP | 1009158 | | 1/1989 |
| JP | 1-214433 | | 8/1989 |
| JP | 2-67374 | | 3/1990 |
| JP | 3-93525 | | 4/1991 |
| JP | 4-353442 | | 12/1992 |
| JP | 6-142799 | | 5/1994 |
| WO | WO 81/01375 | | 5/1981 |
| WO | WO 92/11190 | | 7/1992 |
| WO | WO 93/11743 | | 6/1993 |
| WO | WO 93/11744 | | 6/1993 |
| WO | WO 93/11745 | | 6/1993 |

OTHER PUBLICATIONS

Folke Moren, Aerosol dosage forms and formulations, Aerosols in Medicine, Principles, Diagnosis and Therapy, $2^{nd}$ Ed., pp. 321-350, (1993).

Nothing (Well, Hardly Anything) Sticks to Teflon, The Journal of Teflon, vol. 4, No. 7, pp. 1, 4-6 (1963).

Tetrafluoroethylene Polymers, Encyclopedia of Polymer Science and Engineering, vol. 16, pp. 577-642 (1989).

Kunststoff-Handbuch, Band XI, Section 4.3.6.2, pp. 362-363 (1971).

Kirk-Othmer Encyclopedia of Chemical Technology, Third Edition, vol. 11, pp. 1-49 (1980).

G. Buckton, Surface Energy: Polarity: Metered dose inhaler; Non-aqueous non-polar suspension; Work of adhesion; Work of Cohesion; Spreading coefficient, Centre for Material Sciences, pp. 2-5 and pp. 169-170.

Fluidized Bed Coats Products With FEP RESI, Wilmington, Delaware, vol. 1, No. 4, (Apr. 19).

International Preliminary Report on Patentability for PCT/US2007/025159 issued Aug. 1, 2011, pp. 1-17.

* cited by examiner

METHOD FOR APPLYING A POLYMER COATING TO AN INTERNAL SURFACE OF A CONTAINER

CROSS REFERENCE TO RELATED APPLICATIONS

This application is a continuation of U.S. application Ser. No. 11/952,652, filed Dec. 7, 2007 now U.S. Pat. No. 8,227,027, the subject matter of which is herein incorporated by reference in its entirety.

FIELD OF THE INVENTION

The present invention relates to methods of cleaning and coating at least one surface of a container for storing a medicament using a unique combination of an aqueous cleaner to increase surface wettability and particular aqueous coating compositions to substantially minimize extractable organic compounds while providing effective drug isolation and low propensity for adhesion.

BACKGROUND OF THE INVENTION

Drugs for treating respiratory and nasal disorders are frequently administered in aerosol formulations through the mouth or nose. One widely used method for dispensing such aerosol drug formulations involves preparing a suspension or solution formulation of the drug as a finely divided powder in a liquefied gas known as a propellant. The suspension is stored in a sealed container (or canister) capable of withstanding the pressure required to maintain the propellant as a liquid. The formulation may then be dispersed by activating a dose-metering valve affixed to the container.

The metering valve is typically designed to consistently release a fixed, predetermined mass of the aerosol drug formulation upon each activation. As the formulation is forced from the container through the dose-metering valve by the high vapor pressure of the propellant, the propellant rapidly vaporizes leaving a fast moving cloud of very fine particles of the drug formulation. This cloud of particles is directed into the nose or mouth of the patient by a channeling device such as a cylinder or open ended cone. Concurrently with the activation of the aerosol dose metering valve, the patient inhales the drug particles into the lungs or nasal cavity. Systems of dispensing drugs in this manner are known as "metered dose inhalers" (MDI's).

Patients often rely on medication delivered by MDI's for rapid treatment of respiratory disorders which are debilitating and in some cases, even life threatening, including for example asthma and chronic Obstructive pulmonary disease (COPD). Pharmaceutical compounds for treatment of other conditions or illnesses are targeted for delivery with MDI technology. Therefore, it is essential that the prescribed dose of aerosol medication delivered to the patient consistently meet the specifications claimed by the manufacturer and comply with the requirements of the United States Food & Drug Administration (FDA) and other regulatory authorities. That is, every dose in the canister must be the same within close tolerances.

In some instances, the aerosol drug formulation may tend to adhere to and/or chemically react with the inner surfaces of the MDI, including the canister, metering valve and cap which all make up the MDI system. This can lead to the patient receiving significantly less than the prescribed amount of drug upon each activation of the MDI. Thus, it is often desirable to coat the inner surfaces of the metered dose inhaler, including the metering valve and the inner surface of the container, with a coating material that prevents the drug formulation from adhering to or reacting with the inner surfaces of the MDI.

Previously, fluorine-containing polymers, which have been known for decades to be useful as protective coatings for various articles have more recently been used as protective materials and to coat the inner surfaces of aluminum and aluminum alloy canisters intended for use in storing and administering pulmonary medicament, as described for example in U.S. Pat. No. 6,596,260 to Brugger et al., and in U.S. Pat. Nos. 6,546,928 and 6,532,955 to Ashurst et al., the subject matter of each of which is herein incorporated by reference in its entirety. The use of these fluorine-containing materials to protect the inner surfaces of the containers used to store the drug formulations also allows alternative propellant systems to be used, while at the same time preventing the contamination of the drug formulation with, for example, aluminum or compounds thereof.

However, in some instances, these fluorocarbon polymers may be solvent based rather than aqueous based. Many prior art coating formulations contain solvents that are capable of dissolving the polymer material to make it sprayable. Such prior art solvents include aromatic organic compounds such as n-methyl pyrrolidone, methyl isobutyl ketone, xylene, and/or toluene all of which are suspected carcinogens, among others. In addition, solvent-based cleaning solutions have typically been used to prepare the surfaces to allow coating thereon.

As such, it is also desirable to reduce the quantity of extractable organic compounds used in coating processes (such as solvents) which may contaminate the contents of the container. The use of organic solvents that are flammable has a further drawback in that the equipment used for coating needs to be appropriately protected against fire or explosion hazards. Also, these coatings require the addition of an adhesive to the polymer, otherwise the coating does not adhere sufficiently to the surface. Such adhesives may be costly and time consuming to apply or formulate, and may also be a source of drug contamination.

It is most desirable that any coatings applied to the interior surfaces of the containers, which will necessarily come into contact with the pharmacological formulation, have low available extractable organic compounds, such that there is no interaction between the coating formulation and the pharmacological formulation.

An improved process has been developed for coating metered dose inhaler canisters, including aluminum alloy, deep-drawn metered dose inhaler canisters, using a unique water-based cleaning composition in conjunction with a water-based crosslinked epoxy acrylate or other polymeric internal surface coating material as described herein. This invention has been developed to make the cleaning and coating technology consistent with present environmental regulations and workplace safety requirements, including control of emissions of volatile organic compounds (VOCs). Further, this invention has been developed to reduce the concentration of extractible organic compounds to the lowest practical level.

Prior to the process described herein, the majority of MDI canisters have been solvent-cleaned with a proprietary commercially supplied mixture of hydrocarbons and emulsifiers. While these remove most of the hydrocarbon lubricants used for deep drawing, the resulting surface contains residual oils and fatty acids that prevent wetting with water-based coatings. Prior to coating MDI cans cleaned in this way, they are typically heated above 200° C. to 'burn off' residual hydrocarbons. The remaining surface, however, is not fully wettable with water-based coating materials. Whereas the coating materials described herein might be applied to a surface treated in this manner, optimum adhesion and reduction of residual organic compounds is not assured. A hydrocarbon-free cleaning process was developed to greatly increase the surface wettability of the MDI canister while eliminating downstream contamination from residual hydrocarbons. Examples of a prior art cleaning solvents include Silksol and other types of emulsifiable and semi-emulsifiable hydrocarbon solvent cleaning systems. These typically may contain an aliphatic hydrocarbon solvent, similar to kerosene, and one or more surfactants to promote emulsification with water.

Accordingly, it is an object of the present invention to solve the problems associated with the prior art. It is also an object of the present invention to provide an improved process for coating an internal surface of a medicine storage container with a fluorine-containing polymer, to provide a finer, more uniform and unblemished coating with improved protective properties that requires no adhesive or primer, and which contains a minimum of extractable organic compounds. It is also an object of the present invention to provide a process for coating containers using an aqueous polymer suspension and to overcome the difficulties associated with producing good coatings from an aqueous suspension without using traditional volatile organic hydrocarbon solvents.

SUMMARY OF THE INVENTION

It is an object of the present invention to provide a method of coating surfaces of a container that houses a drug formulation to prevent the adhesion or chemical interaction of the drug formulation with the coated surfaces of the container.

It is another object of the present invention to provide a cleaner composition for cleaning surfaces of such a container prior to applying a coating thereto.

It is another objection of the present invention to provide a water-based cleaning and a water-based coating composition that can be applied to surfaces of a container used to house a drug formulation.

It is another object of the present invention to provide a water-based cleaning and a water-based coating composition that has substantially no extractable organic compounds that can react with the drug formulation.

It is yet another object of the present invention to provide an improved process for coating internal surfaces of a medicament storage container, such as a metered dose inhaler using the compositions of the invention.

It is still another object of the present invention to provide water-based coating composition that provides good adhesion to the internal surfaces of the medicament storage container.

To that end, the present invention relates generally to a method of coating at least one surface of a container for storing a medicament comprising the steps of:
  a) cleaning the at least one surface of the container with an aqueous cleaning solution, wherein the aqueous cleaning solution comprises:
    i) an anionic surfactant; and
    ii) an emulsifier;
  b) coating the cleaned surface with an aqueous coating composition containing an acrylic resin selected from the group consisting of acrylic epoxy resins, acrylic acrylate phenolic resins and fluoropolymer composite acrylic resins, and
  c) crosslinking the coating composition to provide an adherent continuous coating on the at least one surface of the container.

DETAILED DESCRIPTION OF THE PREFERRED EMBODIMENTS

The present invention relates to an improved method of coating interior surfaces of containers, especially containers used for storing medicament formulations, to prevent drug formulations that are stored in the container from adhering to or chemically interacting with surfaces of the container so that a precise metered dose of the drug formulation can be dispensed. Furthermore, the present invention relates to an improved method of coating interior surfaces of containers used to house drug formulations that contain substantially no extractable organic compounds that can react with the drug formulation housed in the container.

In particular, the present invention relates generally to a method of coating at least one surface of a container for storing a medicament or other ingestible non-pharmaceutical product, the method comprising the steps of:
  a) cleaning the at least one surface of the container with an aqueous cleaning solution, wherein the aqueous cleaning solution comprises:
    i) an anionic surfactant; and
    ii) an emulsifier;
  b) coating the cleaned surface with an aqueous coating composition containing an acrylic resin selected from the group consisting of acrylic epoxy resins, acrylic acrylate phenolic resins and fluoropolymer composite acrylic resins, and
  c) crosslinking the coating composition to provide an adherent continuous coating on the at least one surface of the container.

In a preferred embodiment, the process of the invention is used to coat interior surfaces of metered dose inhalers, especially interior surfaces of the canister used to house the drug formulation. The term "metered dose inhaler" (or "MDI") is defined as a unit comprising a container and a crimped drug metering valve situated in the cap. The term "drug metering valve" or "MDI valve" refers to a valve and its associated mechanisms which delivers a precise predetermined amount of a drug or medicament formulation from an MDI upon each activation of the valve. The metered dose inhaler typically also comprising a channeling device such as an actuating device for the valve, and a cylindrical or cone-like passage through which the drug or medicament formulation may be delivered from the filled MDI can via the MDI valve to the nose or mouth of a patient, e.g. a mouthpiece actuator. Metered dose inhalers are well known in the prior art and are described for example in U.S. Pat. No. 5,284,133 to Burns et al, U.S. Pat. No. 5,447,150 to Bacon and in U.S. Pat. No. 6,615,827 to Greenwood et al., the subject matter of each of which is herein incorporated by reference in its entirety.

The term "drug formulation" is defined as a medicament or other pharmacologically active agent in combination with other active or inactive ingredients which may enhance the drug formulation or performance of the MDI system including, but not limited to surfactants, preservatives, flavorings, antioxidants, antiaggregating agents, and cosolvents, e.g., ethanol and diethyl ether.

Preferred drug formulations include for example albuterol, salmeterol, hudesonide, among others, alone or in combination with other active ingredients. Other drug formulations would also be well known to those skilled in the art.

The term "propellants" as used herein refers to pharmacologically inert liquids with boiling points from about room temperature (25° C.) to about −25° C. which singly or in combination exert a high vapor pressure at room temperature. Upon activation of the MDI system, the high vapor pressure of the propellant in the MDI forces a metered amount of drug formulation out through the metering valve then the propellant very rapidly vaporizes dispersing the drug particles. The propellants used in the present invention are low boiling fluorocarbons; such as 1,1,1,2-tetrafluoroethane also known as "propellant 134a" or "P134a" and 1,1,1,2,3,3,3-heptafluoropropane also know as "propellant 227" or "P 227", or hydrofluoroalkane (HFA) among others.

In a preferred embodiment the MDI container and metering valve housing are made of aluminum, an alloy of aluminum, or stainless steel, although other metals not affected by the drug formulation, such as an alloy of copper, or tin plate, may be used. The MDI container may also be fabricated from glass or plastic, although the containers used in the process of the present invention are preferably made of aluminum or an aluminum alloy. Preferred materials include for example aluminum alloys containing magnesium, copper and/or manganese, such as aluminum 5052 or aluminum 3004.

The drug metering valve typically comprises parts that are made of stainless steel, a pharmacologically inert and propellant resistant polymer, such as acetal, polyamide (e.g., Nylon®), polycarbonate, polyester, fluorocarbon polymer (e.g., Teflon®), or a combination of these materials. Additionally, seals and O-rings of various materials (e.g., nitrile rubbers, polyurethane, acetyl resin, fluorocarbon polymers), or other elastomeric or thermoplastic elastomer materials can be employed in and around the valve. Exemplary drug metering values are described for example in U.S. Patent Publication No. 2004/0222244 to Groeger and GB Patent Application No. 2,361,228 to Uroeger, the subject matter of each of which is herein incorporated by reference in its entirety.

Once the deep drawn containers have been fabricated, the containers are subjected to an aqueous cleaning step to removes hydrocarbon lubricants resulting from the deep drawing process and to provide a finished surface with high surface energy and no significant organic extractible compounds based on analysis by gas chromatography. This mildly alkaline cleaning process also increases the specific surface area, thus improving the bond of the subsequently applied coating.

Selection of the cleaner and control of the cleaning water is an important of the process described herein because it is contemplated that in some embodiments, substrates may be simply cleaned and not coated, so the cleaned surface may be suitable for patient contact. For this reason, the cleaning material must be acceptable to the Food and Drug Administration (FDA) for food contact.

A number of cleaners based on environmentally friendly solvents, the most common of which is butoxyethanol, were evaluated. Butoxyethanol is an active ingredient in cleaners such as Luminox® (available from Alconox Corp.) and Simple Green®. While these cleaners were effective at removing the oil, the resulting surface energy was too low to allow proper wetting with aqueous coatings.

Cleaners based on citrus-derived oils, such as limonene and citric acid esters, were also tried, but these also failed to provide high enough surface energy. Similarly, cleaners containing sodium silicate were trialed, however in-process equipment fouling and retention of microscopic silicate deposits made this less desirable.

Accordingly, the cleaning composition described herein was determined to provide a good result. In particular, the cleaning composition of the invention generally comprises:
1) an anionic surfactant; and
2) an emulsifier, In one embodiment, the cleaning composition also comprises at least one of an alkaline salt and a buffer. These components can be added to extend performance and balance the system to prevent corrosion of the aluminum or aluminum alloy. These components can also offer a more stable performance and cleaner longevity.

Optionally, but preferably, the cleaning composition of the invention may also contain a metal chelating agent.

Suitable anionic surfactants include sodium dodecylbenzene sulfonate, alkyl phosphate, alkyl sulfonate, alkyl benzenesulfonate, and sodium di(2-ethylhexyl) sulfosuccinate. Preferably, the anionic surfactant is dodecylbenzene sulfonate. The anionic surfactant is used to penetrate the oil film on the deep drawn cans and to emulsify and disperse the oil in the cleaning bath.

The emulsifier is used to suspend oil drops in the cleaning solution. A preferred emulsifier for use in the composition of the invention is tetrasodium phosphate, which also serves as a pH buffer to extend the cleaning solution stability. While other emulsifying compounds are also usable in the present invention, tetrasodium phosphate is preferred because it has the capability to act as a buffer at the same time.

An alkaline salt can be used to maintain a high pH (which assures stable alkalinity during use) while also binding to magnesium and calcium which are components of hard water. This is further important since the canisters are deep drawn with an alloy that contains magnesium and this is partially removed in the cleaning process. A preferred alkaline salt is sodium carbonate. While other alkaline salts are available, few can be used in human contact applications. Without the inclusion of the alkaline salt, the magnesium may form a precipitate that would contaminate surfaces of the canisters.

Optionally, but preferably, a material that functions as an alkaline emulsifier and a metal chelating agent, such as sodium phosphate, is added to the composition of the invention. The sodium phosphate binds with metals to form compounds that are stable. In the present case, this helps to reduce corrosion and discoloration on the surface of the canisters caused by dissolution of alloying elements from the aluminum. While the sodium phosphate is not a critical ingredient, it does provide process stability. Others alkaline emulsifiers that can be used in the present invention include, by way of example and not limitations, EDTA (ethylenediamene tetraacetic acid), porphine, nitrilo triacetate (NTA), and ethylenediamene, among others.

The cleaning process typically consists of two or three sequential cleaning baths maintained at a temperature between about 25° C. and about 60° C., and more preferably at about 50° C. The pH of the cleaning baths is between 9 and 9.8, most preferably 9.2. Water used to prepare the wash solutions preferably has a conductivity below about 200 μS/cm and hardness is controlled to 0 on the German Hardness scale. The cans are immersed in each bath for a period of about 1 to 5 minutes, but preferably for about two minutes.

In a preferred embodiment, each bath is ultrasonically agitated between about 30 kHz and about 43 kHz, but preferably at about 40 kHz with superimposed sweep frequency of 1 kHz. Oil separation technology is applied and fresh cleaning solution is added on a controlled basis for each tray that is filled with canisters.

In one embodiment, the containers to be cleaned are placed open end upward, edge-to-edge into trays with a capacity of approximately 1000. These trays are lowered edge down into each bath such that each can is filled. The trays are then continuously cycled up and down below each bath surface, then lifted, emptied and refilled in each bath for a repeat of the cleaning cycle between 2 and 4 times, most preferably three times. Other configurations would also be known to one skilled in the art.

Cleaning is followed by several rinse baths, which may include three or four sequential rinse baths. The first may or may not be ultrasonically agitated, but is preferably agitated. The rinse baths are maintained at a temperature of between about 18-27° C., but most preferably at about 25° C. Water hardness is controlled by conductivity measurement to below 50 µS/cm with hardness of 0 on the German hardness scale.

The final rinse bath preferably consists of deionized water, controlled to conductivity between 4 and 20 µS/cm, but most preferably at 5-10 µS/cm with hardness controlled to 0 on the German Hardness scale. This bath has a pH range from 5.8 to 7.0, most preferably 6.8, and the temperature is between 18 and 27° C., but most preferably at 25° C.

The containers are thereafter dried in filtered air in a laminar flow oven.

The cleaned containers were analyzed and found to have the following surface properties.

Organic extractibles were measured by gas chromatography/mass spectrometry (GC/MS) by several sampling methods, as shown in Table 1.

TABLE 1

Total Organic Extractibles

| Sampling method | Total Organics Detected |
|---|---|
| Thermal desorption (ramp to 320° C.) | <1 ppm |
| Ethanol extraction | <1 ppm |
| Methylene chloride extraction | <1 ppm |

Wetting behavior of the cleaned MDI container surface can be determined by contact angle measurement. In one embodiment, the surface energy of the container surface is between about 60 and about 72 dyne-cm, more preferably between about 68 and about 70 dyne-cm.

The cleaning process of the invention eliminates the need for post-cleaning thermal treatment to remove residual organics. This is critical because thermal treatment reduces the strength of the aluminum alloy and also adds to production energy requirements.

Once the cleaning process has been completed, the containers are subjected to a process for coating or lining the interior surface of the container.

A special metered dose inhaler (MDI) has been developed in the process of the present invention for controlled delivery of an active pulmonary or nasal medication. The container comprises a lined container obtainable using the process of the present invention described above.

Various coating compositions have been developed for use on the interior surface of the MDI canister. These coatings are all water-based and must be applied to an aluminum or aluminum alloy surface that is free of hydrocarbon residues. These coatings have been specifically developed to reduce organic extractibles to the lowest extent possible and to be compatible with a range of propellants, including, but not limited to, hydro-fluorocarbon (HFC), and/or hydrofluoroalkane (HFA) and/or ethanol, which can be included as a propellant and/or formulation co-solvent. Furthermore, these coatings are selected to avoid the need for any post-coating thermal treatment above 250° C., thus avoiding strength reduction of the MDI canister through annealing. Because of this, thinwalled MDI canisters having a wall thickness of less than about 0.4 mm can be used while retaining the necessary burst strength.

The coatings are applied to MDI cans, cleaned in the manner described above. In one embodiment, the coating can be applied using internal air spray guns, as described for example in U.S. Pat. No. 7,205,026 to Groeger et al., the subject matter of which is herein incorporated by reference in its entirety. In one embodiment, two to three spray guns are used for each container, one of which sprays in an axial direction, while the other one or two guns spray at an angle offset to 0 degrees by between about 10 and about 30 degrees, more preferably at about 20 degrees. The cans are spinning during coating at a rate between about 3000 and 7000 rpm, most preferably above about 4500 rpm. The spray guns are introduced into the cans at the start of the coating process and spray delivery begins as the spray guns are retracted. The timing of spray delivery and the area of spray application are controlled to assure uniform coverage with a coating of consistent thickness between 4 and 12 micrometers, most preferably between 4 and 8 micrometers. At the time of coating, the containers typically have a temperature between about 20 and 45° C., most preferably between about 30 and 40° C. In another embodiment, the aqueous coating composition can be applied by dip coating or roll coating.

The coating materials usable in the practice of the present invention are based on acrylic polymers and modifications thereof. These coating materials are water-borne emulsions, and are all at least substantially absent any aromatic organic solvents. All have been developed for compatibility with presently used metered dose inhaler propellants, including ethanol as a co-solvent.

The categories of coating materials are described as follows:

(1) E3: acrylic epoxy resins. Examples of suitable acrylic epoxy resins that are usable in the present invention are described in Provisional Patent Application No. 60/012, 210 entitled "Coating Suitable for Medicament Contact" to Schutte et al., filed on the same day as the instant application.

(2) E4: Water-based acrylic acrylate phenolic resins. One suitable source of these acrylic acrylate phenolic resins is Valspar, Inc. This category of coating materials is also described for example in U.S. Pat. No. 7,037,584 to Wind et al., the subject matter of which is herein incorporated by reference in its entirety.

(3) E5: Low surface energy coatings, such as fluoropolymer composite acrylic resins. One suitable source of these low surface energy coatings is Valspar, Inc.

The acrylic resins compositions of the invention consist of 20-40 wt. % of at least one E3, E4 and/or E5 acrylic resin in combination with a mixture of one or more of various alcohols as wetting agents. Examples of alcohols usable as wetting agents in the practice of the present invention include, but are not limited to, n-butyl alcohol (about 2-10 wt. %), 2-butoxyethanol (about 2-10 wt. %), and/or 2-(dimethylamino) ethanol (about 1-5 wt. %), and amyl alcohol, with water as the balance. The concentration of the acrylic resin is adjusted for optimum spray efficiency, surface finish, and thermal desorption, with the optimum between 22 and 27 wt %.

For all of these resins, the crosslinking component is polymerized into the acrylic polymer backbone. In addition, the E5 resin consists additionally of a micro-emulsified aqueous dispersion of a fluoropolymer with a particle size between 0.1 and 1.0 µm, most preferably between 0.1 and 0.3 µm. The fluoropolymer structure may be a monofluoroalkoxy, perfluoroalkoxy, or other fluoropolymer or fluorinated copolymer. The fluoropolymer is added to the base acrylic resin at a concentration between 10 and 50 wt %, most preferably between 15 and 25%. It is generally preferable that the fluoropolymer emulsion not contain a glycolated surfactant or other surfactant that will result in resinous deposits on the interior of the curing oven. Instead, ethoxylated surfactants are generally preferred.

Immediately following the step of applying the coating material, the cans are heated in an oven to a temperature that initiates chemical crosslinking of the coating. The temperature and time at temperature are selected based on measurements of coating crosslinking density and desorption of volatile organic compounds based on measurements with gas chromatography/mass spectrometry.

The E3 and E4 materials are crosslinked at a temperature of between about 210° C. and about 250° C., most preferably between about 220° C. and about 230° C. The time required for crosslinking and thermal desorption is between about 5 and 12 minutes, most preferably between about 8 and 10 minutes. The E5 material is crosslinked at a temperature of between about 210° C. and about 250° C., most preferably between about 230° C. and about 240° C. The time required for crosslinking and thermal desorption of the E5 material is between about 6 and 13 minutes, most preferably between 10 and 12 minutes.

In one embodiment, the coating materials of the invention can be blended with various colorants to provide a basis for anti-counterfeiting. With a uniquely colored interior surface that is not apparent from the outside, the interior surface can be made unique to a particular manufacturer and/or product. Thus, the container is in effect color-coded so that it cannot be filled with the wrong pharmaceutical formulation. Colorants consist of various phthalocene and metal oxide compounds as well as other compounds that are qualified under 21 CFR 175.300 for use in food contact applications. In other embodiments of the invention, the coating formulation can be clear, opaque or translucent.

Furthermore, while the coating compositions have been described herein for coating interior surfaces of an MDI container, the coating compositions may also be used to treat the metering valve of the MDI. Prior art methods of Various surface properties of examples of coating materials of the invention are provided below in Table 2.

TABLE 2

Measurement of Surface Properties.

| Measurement | E3 | E4 | E5 |
|---|---|---|---|
| WACO range, mA @6.3 V | 5-20 | 5-20 | 0-10 |
| Surface energy dyne~cm | 3-5 | 4-6 | 1-2 |
| Adhesion and flexibility (reverse bend, 180° reverse, then 180° forward | Pass | Pass | Pass |
| Extractibles (ethanol 60° C., 30 days) | None detectable | None detectable | None detectable |
| Extractibles (thermal desorption, 220° C.) | <1 ppm polymer fragments | <1 ppm polymer fragments | <1 ppm polymer fragments |
| Leachables, water, 60° C., 30 days | None detectable | None detectable | None detectable |
| Permeability, based on acidified CuSO4 contact, minutes | 2-10 | >10 | >20 |
| Surface roughness, RMS | 0.1-0.4 μm | 0.1-.3 μm | 0.1-0.5 μm |

TABLE 2-continued

Measurement of Surface Properties.

| Measurement | E3 | E4 | E5 |
|---|---|---|---|
| Propellant compatibility | CFC, HFC HFA, ethanol | CFC, HFC, HFA, ethanol | CFC, HFC HFA, ethanol |

(1) WACO testing was conducted with a Wilkens Andersen Enamel Rater II testing device, with 6.3 Volts DC, tested for 4.0 seconds. Current was measured with cans completely filled with a sodium chloride solution. This is made with 10 wt % sodium chloride dissolved in deionized water.
(2) Surface energy was determined by measurement of contact angle between the coated can surface and water droplets of controlled volume. A calibrated microscope was used for these measurements.
(3) Extractibles were measured using gas chromatography using a mass spectrometer detector (GC/MS). Solvent extraction with pure (99.9%) anhydrous ethanol and thermal desorption were used as sampling methods. Leachables were measured similarly, after water removal and dissolution of the remains in methylene chloride.
(4) Copper sulphate resistance testing was conducted with a typical test solution consisting of approximately 0.2 wt % copper sulphate in water, acidified slightly by addition of approximately 0.02 wt % hydrochloric acid. Breakdown of the coating is determined by onset of corrosive interaction between the solution and the aluminum.
(5) Surface roughness was measured with a profilometer on strips cut from coated cans. These were not flattened for measurement.
(6) Propellant compatibility was determined through observation for any structural changes in the coating that included changes in color, transparency, swelling, loss of adhesion, and identification of polymer fragments in the propellant, as determined by GC/MS.

In one embodiment, the E3, E4 and E5 coating materials described herein can also be applied to exterior surfaces of the containers. Complete removal of hydrocarbons from the surface of cans during cleaning results in high friction between cans, due to properties inherent in most aluminum alloys. High interfacial friction can be detrimental when conveying cans through automated handling equipment, where high friction interferes with bowl-feeding and other operations. Thus, applying the coating materials of the invention as an exterior surface coating can help reduce the high canto-can friction resulting from the cleaning process of the invention. As discussed above, the conventional cleaning process leaves an oily surface, while the cleaning process described herein leaves nothing but bare metal (i.e., aluminum). Thus, it has been found that the composition of the invention can be used to pre-coat the entire container via immersion in a dilute solution with the same coating material as is applied to the interior surfaces of the container.

Accordingly, in one embodiment, the E3, E4, and E5 coating materials can be applied simultaneously to the exterior and interior surfaces of the containers by immersion immediately following cleaning. The coating materials are first diluted with deionized. water to between 10 and 20% of their original concentration, which provides a very thin reduced friction coating on the interior and exterior surface. The containers are then heated to approximately 200° C. for about 2-3 minutes to provide crosslinking of the coating. Thereafter, the containers can then be stored and subsequently internally coated in the aforementioned manner with the same coating material.

In an alternate embodiment, the coating materials are applied to the external surface using roll-printing or gravure printing to print the E3, E4, or E5 coating material on the exterior surfaces of the can. This process has been found to work especially well for the E5 coating materials. This coating is applied directly to the outer surface only by means of fixing individual cans and rotating each over a stationary pad that is saturated with coating material, or by transfer of the can to adjacent, counter-rotating rubber rollers that are saturated with coating material. These rubber rollers are saturated with coating material by rolling through an open reservoir of coating material or by other means. Following coating application, these cans are secured on the neck end and heated in an oven to 200° C. for 2-3 minutes, most preferably 2 minutes. External surface coating may be completed before or following interior surface coating, but is preferably done prior to the step of interior surface coating.

Furthermore, while the present invention has been described herein for coating the container portion of a metered dose inhaler, the process described herein can also be used for cleaning and coating metering valve components of the metered dose inhaler. That is, the drug-contact surfaces can be coated to provide a low adhesion surface and barrier against contact with aluminum metal that may contaminate and/or degrade drug formulations.

Furthermore, the invention may also be used for coating other substrates where it is desired to have low-extractable organics and high adhesion of the subsequently applied coating. Non-limiting examples of components that may be coated using the process of the present invention include toothpaste tubes, ointment tubes and food tubes. Thus, it is contemplated that the process of the invention can be used for cleaning and coating of medicament or ointment tubes. These tubes are presently impact-extruded and internally coated with solvent-based coating materials. The materials of the invention can thus be used to clean and coat the drug contact internal surface and provide an inert barrier between the formulation and the metal surface of the tube.

Other product tubes, such as toothpaste and other ingestible, non-pharmaceutical products could also be cleaned and coated using the process of the present invention.

It is also contemplated by the present invention that the cleaning and coating steps may be performed on the stock aluminum or aluminum alloy strip material before any other processing steps. That is, the cleaning and coating steps may be performed prior to the deep drawing process for creating the deep drawn containers.

While the invention has been described above with reference to specific embodiments thereof, it is apparent that many changes, modifications, and variations can be made without departing from the inventive concept disclosed here. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A cleaned container for storing a medicament or other ingestible non-pharmaceutical composition, wherein at least a portion of an interior surface of the container is coated with an aqueous cleaning solution comprising an anionic surfactant, an emulsifier, and sodium carbonate and then rinsed, wherein said the at least the portion of the interior surface of the container has a surface energy of between about 60 and about 72 dyne-cm and wherein the cleaned surface is at least substantially free of hydrocarbon residues.

2. The cleaned container according to claim 1, wherein the anionic surfactant is selected from the group consisting of sodium dodecylbenzene sulfonate, alkyl phosphate alkyl sulfonate, alkyl benzenesulfonate and sodium di(2-ethylhexyl) sulfosuccinate.

3. The cleaned container according to claim 2, wherein the anionic surfactant comprises dodecylbenzene sulfonate.

4. The cleaned container according to claim 1, wherein the emulsifier comprises tetrasodium phosphate.

5. The cleaned container according to claim 1, wherein the aqueous cleaning solution is hydrophobic.

6. The cleaned container according to claim 1, wherein the at least one surface of the container comprises a material selected from the group consisting of aluminum, aluminum alloy and stainless steel.

7. The cleaned container according to claim 1, wherein the aqueous cleaning solution comprises at least one of an additional alkaline salt and a buffer.

8. The cleaned container according to claim 1, wherein the aqueous cleaning solution comprises an alkaline emulsifier selected from the group consisting of sodium phosphate, ethylenediamine tetraacetic acid, porphine, nitrilo triacetate and ethylenediamine.

9. The cleaned container according to claim 8, wherein the alkaline emulsifier comprises sodium phosphate.

10. The cleaned container according to claim 1, wherein said the at least the portion of the interior surface of the container has a surface energy of between about 68 and about 70 dyne-cm.

\* \* \* \* \*